United States Patent
Odaka et al.

(10) Patent No.: US 6,329,403 B1
(45) Date of Patent: Dec. 11, 2001

(54) PHARMACEUTICAL COMPOSITION FOR THE TREATMENT OF DIABETES

(75) Inventors: Hiroyuki Odaka, Kobe; Masahiro Yamane, Suita, both of (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/380,059

(22) PCT Filed: Jun. 29, 1999

(86) PCT No.: PCT/JP99/03496

§ 371 Date: Aug. 25, 1999

§ 102(e) Date: Aug. 25, 1999

(87) PCT Pub. No.: WO00/00195

PCT Pub. Date: Jan. 6, 2000

(30) Foreign Application Priority Data

Jun. 30, 1998 (JP) .................................................. 10-183700

(51) Int. Cl.$^7$ .......................... A61K 31/44; A61K 31/135
(52) U.S. Cl. .......................... 514/342; 514/369; 514/374; 514/399; 514/646; 514/866
(58) Field of Search ..................... 514/342, 369, 514/374, 399, 866, 646

(56) References Cited

U.S. PATENT DOCUMENTS 6,174,925 * 1/2001 Bailey et al. ........................ 514/646

FOREIGN PATENT DOCUMENTS

| 0440333 A | 8/1991 | (EP) . |
| 0516349-A | 12/1992 | (EP) . |
| 0749751-A | 12/1996 | (EP) . |
| 05 148196 A | 6/1993 | (JP) . |
| 09 067271 A | 3/1997 | (JP) . |
| WO 93/03724 | 3/1993 | (WO) . |
| WO 97/27847 | 8/1997 | (WO) . |

OTHER PUBLICATIONS

A. Okuno et al., "Effects of Thiazolidine Derivatives on Zucker Fatty Rat Adipose Tissue" *Diabetes Frontier* vol. 8, 1997 pp. 499–501 (With its English translation).

A.A. Kheir El–Din et al., "Possible Interactions of Some Anorexigenic Drugs . . . " *Egypt J. Pharm. Sci.* vol. 29, No. 1–4, pp. 355–366 (1988).

* cited by examiner

*Primary Examiner*—Rebecca Cook
(74) *Attorney, Agent, or Firm*—Mark Chao; Elaine M. Ramesh

(57) ABSTRACT

A pharmaceutical composition which comprises an insulin sensitizer in combination with an anorectic, which is useful as an agent for preventing or treating diabetes.

19 Claims, No Drawings

PHARMACEUTICAL COMPOSITION FOR THE TREATMENT OF DIABETES

This is a 371 of PCT /JP99/03496 filed Jun. 29, 1999.

TECHNICAL FIELD

The present invention relates to a pharmaceutical composition which comprises an insulin sensitizer (insulin resistance-improving agent) in combination with an anorectic. The pharmaceutical composition of the present invention can be used as an agent for preventing or treating diabetes, etc.

BACKGROUND ART

Examples of prior art references which relate to an insulin sensitizer or an anorectic are mentioned below.
1) JP-A H9(1997)-67271 describes "a pharmaceutical composition an insulin sensitivity enhancer in combination with at least one member selected from the group consisting of α-glucosidase inhibitor, an aldose reductase inhibitor, a biguanide, a statin compound, a squalene synthesis inhibitor, a fibrate compound, a LDL catabolism enhancer and an angiotensin converting enzyme inhibitor".
2) JP-A H5(1993)-148196 describes that "a pharmaceutical composition comprising 4-[2-(2-hydroxy-2-phenylethylamino)ethoxy]phenyl acetic acid, or its precursor or its pharmaceutically acceptable salt and a pharmaceutically acceptable carrier" may contain "an anorectic, a vitamin, a hypotensive drug and an blood glucose lowering agent, for instance, sulfonylureas, biguanides and thiazolidinediones".
3) Diabetes Frontier, Vol.8, p.499 (1997) describes that "CL316243 completely inhibited the weight gain in brown adipose tissues caused by troglitazone" when CL316243 (β 3 adrenergic receptor antagonist) and troglitazone were administered to obese rats.
4) WO93/3724 describes that 3-Guanidinopropionic acid (3-GPA) antagonizes in a dose-dependent manner the weight gain that occurs in obese, diabetic KKA$^Y$ mice that are treated with pioglitazone hydrochloride, an insulin sensitizing agent.
5) Egypt. J. Pharm. Sci., vol.29, No.1–4, pp.355–366(1988) describes "interactions of some anorexigenic drugs with tolubutamide in normal and diabetic rats".
6) WO97/27847 describes that "acetylphenols which are useful as antiobesity and antidiabetic compounds" can be used together with "fenfluramines, dexfenfluramines, phentiramines, β 3 adrenergic receptor agonists".

These prior art references do not specifically describe or suggest combining an insulin sensitizer with an anorectic, and effects of such combination.

The origin of noninsulin-dependent diabetes mellitus (NIDDM) includes insufficient insulin action in the liver and peripheral tissues (insulin resistance) as well as insulin secretion deficiency in the pancreas. The onset of the insulin resistance is highly affected by the present satiety environment such as stress and obesity, and alimentotherapy is firstly employed for reduction of the insulin resistance. However, observance and continuation of the alimentotherapy is accompanied by mental pains of patients, and in many cases does not provide the expected results. Therefore, an insulin sensitizer is employed as a subsidiary drug for the alimentotherapy, and an anti-obesity drug is employed in obese patients.

The insulin sensitizer strengthens insulin action to lower blood sugar in diabetic patients.

In obesity, the number of insulin receptors in fatty cells themselves are reduced because of hypertrophy of fatty tissues, further, insulin resistance is strengthened by accelerated secretion of insulin resistance-causing cytokines such as TNF-α. Increase of the amount of required insulin accelerates insulin secretion in the pancreas. As a result, in most cases, obesity is accompanied by hyperinsulinemia or hyperlipidemia.

On the other hand, an anorectic do not result in lowering blood glucose in many cases, although they reduce body fat. The anorectic is known to possess side effects such as dependence, hydrodipsia, constipation, nausea, emesis, gastric discomfort, stomach flatulence, dizziness, palpitation, eruption, increase of GTO or GPT, sleep disturbance, etc.

Development of excellent drugs which are sufficiently improved as a medicine having an excellent diabetic treatment effect without apparent detection of side effects is desired.

DISCLOSURE OF INVENTION

As a result of various studies of medicinal properties such as a diabetic treatment effect, a side effect, etc., the present inventors combined an insulin sensitizer with an anorectic for the first time, and found, for the first time, that such combination unexpectedly provided quite excellent properties as a medicine such as an excellent blood sugar lowering effect, no apparent detection of side effects, etc. Based on this finding, the present inventors have completed the present invention.

Namely, the present invention relates to
(1) a pharmaceutical composition which comprises an insulin sensitizer in combination with an anorectic;
(2) a pharmaceutical composition according to the above (1), wherein the insulin sensitizer is a compound of the formula:

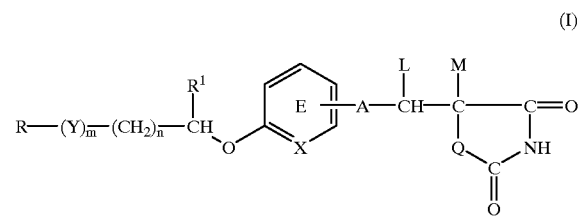

wherein R represents a hydrocarbon group or a heterocyclic group, each of which may be substituted; Y represents a group of the formula: —CO—, —CH(OH)— or —NR$^3$— where R$^3$ represents an alkyl group that may be substituted; m is 0 or 1; n is 0, 1 or 2; X represents CH or N; A represents a chemical bond or a bivalent aliphatic hydrocarbon group having 1 to 7 carbon atoms; Q represents oxygen or sulfur; R$^1$ represents hydrogen or an alkyl group; ring E may have further 1 to 4 substituents, which may form a ring in combination with R$^1$; L and M respectively represent hydrogen or may be combined with each other to form a chemical bond; or a salt thereof;
(3) a pharmaceutical composition according to the above (1), wherein the insulin sensitizer is pioglitazone hydrochloride, troglitazone, rosiglitazone or 4-[4-[2-(5-methyl-2-phenyloxazol-4-yl)ethoxy]benzyl]isoxazolidin-3,5-dione;
(4) a pharmaceutical composition according to the above (2), wherein the compound of the formula (I) or salt thereof is pioglitazone hydrochloride;
(5) a pharmaceutical composition according to the above (1), wherein the anorectic is a central anorectic;

(6) a pharmaceutical composition according to the above (5), wherein the central anorectic is mazindol;
(7) a pharmaceutical composition according to the above (1), wherein the insulin sensitizer is pioglitazone hydrochloride and the anorectic is mazindol;
(8) a pharmaceutical composition according to the above (1), which is for preventing or treating diabetes;
(9) a pharmaceutical composition according to the above (8), wherein the diabetes is noninsulin-dependent diabetes mellitus;
(10) a pharmaceutical composition according to the above (2), wherein the compound of the formula (I) or salt thereof is troglitazone;
(11) a pharmaceutical composition according to the above (2), wherein the compound of the formula (I) or salt thereof is rosiglitazone or its maleate;
(12) a pharmaceutical composition according to the above (1), which is for preventing or treating diabetic complications;
(13) a pharmaceutical composition according to the above (1), which is for preventing or treating impaired glucose tolerance;
(14) a pharmaceutical composition which comprises an insulin sensitizer and is used in combination with an anorectic;
(15) a method for preventing or treating diabetes in a mammal in need thereof, which comprises administering to said mammal an effective amount of an insulin sensitizer in combination with an anorectic;
(16) a method for preventing or treating diabetic complications in a mammal in need thereof, which comprises administering to said mammal an effective amount of an insulin sensitizer in combination with an anorectic;
(17) a method for preventing or treating impaired glucose tolerance in a mammal in need thereof, which comprises administering to said mammal an effective amount of an insulin sensitizer in combination with an anorectic;
(18) use of an insulin sensitizer for the manufacture of a pharmaceutical preparation for treating diabetes which is used in combination with an anorectic;
(19) use of an insulin sensitizer for the manufacture of a pharmaceutical preparation for treating diabetic complications which is used in combination with an anorectic;
(20) use of an insulin sensitizer for the manufacture of a pharmaceutical preparation for treating impaired glucose tolerance which is used in combination with an anorectic; and
(21) a method for reducing the amount of an insulin sensitizer or/and an anorectic administered to a diabetic mammal, which comprises administering to said mammal an effective amount of them.

The insulin sensitizer used in the present invention means any and all drugs that restore the impaired insulin receptor function and improve insulin resistance. Specific examples of the insulin sensitizer include the above-mentioned compound represented by the formula (I) or a salt thereof.

Referring to the formula (I), examples of the hydrocarbon group in the hydrocarbon group that may be substituted for R include aliphatic hydrocarbon groups, alicyclic hydrocarbon groups, alicyclic-aliphatic hydrocarbon groups, aromatic-aliphatic hydrocarbon groups, and aromatic hydrocarbon groups. The number of carbon atoms constituting such hydrocarbon groups is preferably 1 to 14.

The aliphatic hydrocarbon group is preferably a $C_{1-8}$ aliphatic hydrocarbon group. Examples of the aliphatic hydrocarbon group includes saturated $C_{1-8}$ aliphatic hydrocarbon groups (e.g. alkyl groups, etc.) such as methyl, ethyl, propyl, isopropyl, butyl, isobutyl, sec-butyl, t-butyl, pentyl, isopentyl, neopentyl, t-pentyl, hexyl, isohexyl, heptyl, and octyl; and unsaturated $C_{2-8}$ aliphatic hydrocarbon groups (e.g. alkenyl groups, alkadienyl groups, alkynyl groups, alkadiynyl groups, etc.) such as vinyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, and 1-octynyl.

The alicyclic hydrocarbon group is preferably a $C_{3-7}$ alicyclic hydrocarbon group. Examples of the alicyclic hydrocarbon group include saturated $C_{3-7}$ alicyclic hydrocarbon groups (e.g. cycloalkyl groups, etc.) such as cyclopropyl, cyclobutyl, cyclopentyl, cyclohexyl, cycloheptyl, etc. and unsaturated $C_{5-7}$ alicyclic hydrocarbon groups (e.g. cycloalkenyl groups, cycloalkadienyl groups, etc.) such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, and 2,4-cycloheptadienyl.

The alicyclic-aliphatic hydrocarbon group is a group consisting of the above-described alicyclic hydrocarbon group and aliphatic hydrocarbon group (e.g. cycloalkylalkyl groups, cycloalkenyl-alkyl groups, etc.) and is preferably a $C_{4-9}$ alicyclic-aliphatic hydrocarbon group.

Examples of the alicyclic-aliphatic hydrocarbon group include cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl, etc.

The aromatic-aliphatic hydrocarbon group is preferably a $C_{7-13}$ aromatic-aliphatic hydrocarbon group (e.g. aralkyl groups, etc.). Examples of the aromatic-aliphatic hydrocarbon group include $C_{7-9}$ phenylalkyl such as benzyl, phenethyl, 1-phenylethyl, 3-phenylpropyl, 2-phenylpropyl and 1-phenylpropyl; $C_{11-13}$ naphthylalkyl such as α-naphthylmethyl, α-naphthylethyl, β-naphthylmethyl, and β-naphthylethyl.

The aromatic hydrocarbon group is preferably a $C_{6-14}$ aromatic hydrocarbon group (e.g. aryl groups, etc.). Examples of the aromatic hydrocarbon group include phenyl and naphthyl (α-naphthyl, β-naphthyl).

Referring to the formula (I), examples of the heterocyclic group in a heterocyclic group that may be substituted for R is a 5- to 7-membered heterocyclic group containing 1 to 4 hetero-atoms selected from oxygen, sulfur, and nitrogen in addition to carbon as ring members or a condensed cyclic group. Examples of the condensed ring include one consisting of such a 5- to 7-membered heterocyclic group with a 6-membered ring containing 1 or 2 nitrogen atoms, a benzene ring, or a 5-membered ring containing one sulfur atom.

Examples of the heterocyclic group includes 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-oxadiazol-5-yl, 1,2,4-triazol-3-yl, 1,2,3-triazol-4-yl, tetrazol-5-yl, benzimidazol-2-yl, indol-3-yl, 1H-indazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin- 2-yl, 1H-imidazo[4,5-b]pyrazin-2-yl, benzopyranyl and dihydrobenzopyranyl. The preferred heterocyclic group is pyridyl, oxazolyl or thiazolyl group.

Referring to the formula (I), the hydrocarbon group and heterocyclic group for R may respectively have 1 to 5, preferably 1 to 3 substituents at substitutable positions. Such substituents include for example aliphatic hydrocarbon groups, alicyclic hydrocarbon groups, aryl groups, aromatic heterocyclic groups, non-aromatic heterocyclic groups, halogen, nitro, amino group that may be substituted, acyl group that may be substituted, hydroxy group that may be substituted, thiol group that may be substituted, carboxyl group that may be esterified, amidino, carbamoyl, sulfamoyl, sulfo, cyano, azido, and nitroso.

Examples of the aliphatic hydrocarbon group include straight-chain or branched aliphatic hydrocarbon groups having 1 to 15 carbon atoms, such as alkyl groups, alkenyl groups, and alkynyl groups.

The preferred alkyl group is a $C_{1-10}$ alkyl group, such as methyl, ethyl, propyl, isopropyl, butyl, isobutyl, sec-butyl, t-butyl, pentyl, isopentyl, neopentyl, t-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, and decyl.

The preferred alkenyl group is a $C_{2-10}$ alkenyl group, such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

The preferred alkynyl group is a $C_{2-10}$ alkynyl group, such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, and 5-hexynyl.

Examples of the alicyclic hydrocarbon group includes saturated and unsaturated alicyclic hydrocarbon groups having 3 to 12 carbon atoms, such as cycloalkyl groups cycloalkenyl groups, and cycloalkadienyl groups.

The preferred cycloalkyl group is a $C_{3-10}$ cycloalkyl group, such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, and bicyclo[4.3.1]decyl.

The preferred cycloalkenyl group is a $C_{3-10}$ cycloalkenyl group, such as 2-cyclopenten-1-yl, 3-cyclopenten-1-yl, 2-cyclohexen-1-yl, and 3-cyclohexen-1-yl.

The preferred cycloalkadienyl group is a $C_{4-10}$ cycloalkadienyl group, such as 2,4-cyclopentadien-1-yl, 2,4-cyclohexadien-1-yl, and 2,5-cyclohexadien-1-yl.

The preferred aryl group is a $C_{6-14}$ aryl group, such as phenyl, naphthyl (1- naphthyl, 2-naphthyl), anthryl, phenanthryl, and acenaphthylenyl.

The preferred aromatic heterocyclic group includes monocyclic aromatic heterocyclic groups, such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, and triazinyl; and condensed aromatic heterocyclic groups, such as benzofuranyl, isobenzofuranyl, benzo [b] thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, and 1,2,4-triazolo[4,3-b]pyridazinyl.

The preferred non-aromatic heterocyclic group includes oxiranyl, azetidinyl, oxetanyl, thietanyl, pyrrolidinyl, tetrahydrofuryl, thiolanyl, piperidyl, tetrahydropyranyl, morpholinyl, thiomorpholinyl, piperazinyl, pyrrolidino, piperidino, morpholino, and thiomorpholino.

Examples of the halogen include fluorine, chlorine, bromine, and iodine.

Referring to the amino group that may be substituted, examples of the substituted amino group include N-mono-substituted groups and N,N-di-substituted amino groups. Examples of the substituted amino group include amino groups having one or two substituents selected from the group consisting of $C_{1-10}$ alkyl groups, $C_{2-10}$ alkenyl groups, $C_{2-10}$ alkynyl groups, aromatic groups, heterocyclic groups or $C_{1-10}$ acyl groups (e.g. methylamino, dimethylamino, ethylamino, diethylamino, dibutylamino, diallylamino, cyclohexylamino, phenylamino, N-methyl-N-phenylamino, acetylamino, propionylamino, benzoylamino, nicotinoylamino, etc.).

Examples of the acyl group in the acyl groups that may be substituted include $C_{1-13}$ acyl groups, for example, $C_{1-10}$ alkanoyl groups, $C_{3-10}$ alkenoyl groups, $C_{4-10}$ cycloalkanoyl groups, $C_{4-10}$ cycloalkenoyl groups, $C_{6-12}$ aromatic carbonyl groups.

Preferred examples of the $C_{1-10}$ alkanoyl groups include formyl, acetyl, propionyl, butyryl, isobutyryl, valeryl, isovaleryl, pivaloyl, hexanoyl, heptanoyl, and octanoyl.

Preferred examples of the $C_{3-10}$ alkenoyl groups include acryloyl, methacryloyl, crotonoyl, and isocrotonoyl.

Preferred examples of the $C_{4-10}$ cycloalkanoyl groups include cyclobutanecarbonyl, cyclopentanecarbonyl, cyclohexanecarbonyl, and cycloheptanecarbonyl.

Preferred examples of the $C_{4-10}$ cycloalkenoyl groups include 2-cyclohexenecarbonyl.

Preferred examples of the $C_{6-12}$ aromatic carbonyl groups include benzoyl, naphthoyl, and nicotinoyl.

Examples of the substituents in the substituted acyl groups include $C_{1-3}$ alkyl groups, $C_{1-3}$ alkoxy groups, halogen (e.g. chlorine, fluorine, bromine, etc.), nitro, hydroxy, and amino.

Referring to the hydroxy group that may be substituted, examples of the substituted hydroxy includes alkoxy groups, cycloalkyloxy groups, alkenyloxy groups, cycloalkenyloxy groups, aralkyloxy groups, acyloxy groups, and aryloxy groups.

The preferred alkoxy group includes $C_{1-10}$ alkoxy groups, such as methoxy, ethoxy, propoxy, isopropoxy, butoxy, isobutoxy, sec-butoxy, t-butoxy, pentyloxy, isopentyloxy, neopentyloxy, hexyloxy, heptyloxy, and nonyloxy.

The preferred cycloalkyloxy group includes $C_{3-10}$ cycloalkyloxy groups, such as cyclobutoxy, cyclopentyloxy, and cyclohexyloxy.

The preferred alkenyloxy group includes $C_{2-10}$ alkenyloxy groups, such as allyloxy, crotyloxy, 2-pentenyloxy, and 3-hexenyloxy.

The preferred cycloalkenyloxy group includes $C_{3-10}$ cycloalkenyloxy groups, such as 2-cyclopentenylmethoxy, and 2-cyclohexenylmethoxy.

The preferred aralkyloxy group includes $C_{7-10}$ aralkyloxy groups, such as phenyl-$C_{1-4}$ alkyloxy (e.g. benzyloxy, phenethyloxy, etc.).

The preferred acyloxy group includes $C_{2-13}$ acyloxy groups, more preferably $C_{2-4}$ alkanoyloxy groups (e.g. acetyloxy, propionyloxy, butyryloxy, isobutyryloxy, etc.).

The preferred aryloxy group includes $C_{6-14}$ aryloxy groups, such as phenoxy, and naphthyloxy. This aryloxy group may have 1 or 2 substituents. Examples of the substituents include halogen (e.g. chlorine, fluorine, bromine, etc.). Examples of the substituted aryloxy group includes 4-chlorophenoxy.

Referring to the thiol group that may be substituted, examples of the substituted thiol group include alkylthio groups, cycloalkylthio groups, alkenylthio groups, cycloalkenylthio groups, aralkylthio groups, acylthio groups, and arylthio groups.

The preferred alkylthio group includes $C_{1-10}$ alkylthio groups, such as methylthio, ethylthio, propylthio, isopropylthio, butylthio, isobutylthio, sec.-butylthio, t.-butylthio, pentylthio, isopentylthio, neopentylthio, hexylthio, heptylthio, and nonylthio.

The preferred cycloalkylthio group includes $C_{3-10}$ cycloalkylthio groups such as cyclobutylthio, cyclopentylthio, and cyclohexylthio.

The preferred alkenylthio group includes $C_{2-10}$ alkenylthio groups, such as allylthio, crotylthio, 2-pentenylthio, and 3-hexenylthio.

The preferred cycloalkenylthio group includes $C_{3-10}$ cycloalkenylthio groups such as 2-cyclopentenylthio, and 2-cyclohexenylthio.

The preferred aralkylthio group includes $C_{7-10}$ aralkylthio groups, such as phenyl-$C_{1-4}$ alkylthio (e.g. benzylthio, phenethylthio, etc.).

The acylthio group is preferably a $C_{2-13}$ acylthio group, more preferably a $C_{2-4}$ alkanoylthio group (e.g. acetylthio, propionylthio, butyrylthio, isobutyrylthio, etc.).

The preferred arylthio group includes $C_{6-14}$ arylthio groups, such as phenylthio, and naphthylthio. This arylthio group may have 1 or 2 substituents. Examples of the substituents include halogen (e.g. chlorine, fluorine, bromine, etc.). Examples of the substituted arylthio group includes 4-chlorophenylthio.

The carboxyl group that may be esterified includes alkoxycarbonyl groups, aralkyloxycarbonyl groups, and aryloxycarbonyl groups.

The preferred alkoxycarbonyl group includes $C_{2-5}$ alkoxycarbonyl groups, such as methoxycarbonyl, ethoxycarbonyl, propoxycarbonyl, and butoxycarbonyl.

The preferred aralkyloxycarbonyl group includes $C_{8-10}$ aralkyloxycarbonyl groups, such as benzyloxycarbonyl.

The preferred aryloxycarbonyl group includes $C_{7-15}$ aryloxycarbonyl groups, such as phenoxycarbonyl, and p-tolyloxycarbonyl.

The preferred substituent on the hydrocarbon or heterocyclic group for R includes $C_{1-10}$ alkyl groups, aromatic heterocyclic groups, and $C_{6-14}$ aryl groups. Particularly preferred is $C_{1-3}$ alkyl, furyl, thienyl, phenyl, or naphthyl.

Referring to the formula (I), when the substituent on the hydrocarbon or heterocyclic group for R is an alicyclic hydrocarbon group, an aryl group, an aromatic heterocyclic group, or a non-aromatic heterocyclic group, this substituent may further have one or more, preferably 1 to 3 suitable substituents. Examples of such substituents include $C_{1-6}$ alkyl groups, $C_{2-6}$ alkenyl groups, $C_{2-6}$ alkynyl groups, $C_{3-7}$ cycloalkyl groups, $C_{6-14}$ aryl groups, aromatic heterocyclic groups (e.g. thienyl, furyl, pyridyl, oxazolyl, thiazolyl, etc.), non-aromatic heterocyclic groups (e.g. tetrahydrofuryl, morpholino, thiomorpholino, piperidino, pyrrolidino, piperazino, etc.), $C_{7-9}$ aralkyl groups, amino, N-mono-$C_{1-4}$ alkylamino groups, N,N-di-$C_{1-4}$ alkylamino groups, $C_{2-8}$ acylamino groups (e.g. acetylamino, propionylamino, benzoylamino, etc.), amidino, $C_{2-8}$ acyl groups (e.g. $C_{2-8}$ alkanoyl groups, etc.), carbamoyl, N-mono-$C_{1-4}$ alkylcarbamoyl groups, N,N-di-$C_{1-4}$ alkylcarbamoyl groups, sulfamoyl, N-mono-$C_{1-4}$ alkylsulfamoyl groups, N,N-di-$C_{1-4}$ alkylsulfamoyl groups, carboxyl, $C_{2-8}$ alkoxycarbonyl groups, hydroxy, $C_{1-4}$ alkoxy groups, $C_{2-5}$ alkenyloxy groups, $C_{3-7}$ cycloalkyloxy groups, $C_{7-9}$ aralkyloxy groups, $C_{6-14}$ aryloxy groups, mercapto, $C_{1-4}$ alkylthio groups, $C_{7-9}$ aralkylthio groups, $C_{6-14}$ arylthio groups, sulfo, cyano, azido, nitro, nitroso, and halogen.

In the formula (I), R is preferably a heterocyclic group that may be substituted. More preferably, R is pyridyl, oxazolyl, or thiazolyl group, which may have 1 to 3 substituents selected from the group consisting of $C_{1-3}$ alkyl, furyl, thienyl, phenyl, and naphthyl.

Referring to the formula (I), Y represents —CO—, —CH(OH)— or —NR$^3$— where R$^3$ represents an alkyl group that may be substituted. Preferred is —CH(OH)— or —NR$^3$—. Examples of an alkyl group in the alkyl group that may be substituted for R$^3$, include $C_{1-4}$alkyl groups, such as methyl, ethyl, propyl, isopropyl, butyl, isobutyl, sec. -butyl, and t.-butyl. Examples of the substituent include halogen (e.g. fluorine, chlorine, bromine, iodine), $C_{1-4}$ alkoxy groups (e.g. methoxy, ethoxy, propoxy, butoxy, isobutoxy, sec.-butoxy, t.-butoxy, etc.), hydroxy, nitro, and $C_{1-4}$acyl groups (e.g. formyl, acetyl, propionyl, etc.).

The symbol m represents 0 or 1, and is preferably 0.

The symbol n represents 0, 1 or 2, and is preferably 0 or 1.

X represents CH or N, and is preferably CH.

Referring to the formula (I), A represents a chemical bond or a bivalent aliphatic hydrocarbon group having 1 to 7 carbon atoms. This aliphatic hydrocarbon group may be straight-chain or branched and may further be saturated or unsaturated. Thus, for example, —CH$_2$—, —CH(CH$_3$)—, —(CH$_2$)$_2$—, —CH(C$_2$H$_5$)—, —(CH$_2$)$_3$—, —(CH$_2$)$_4$—, —(CH$_2$)$_5$—, —(CH$_2$)$_6$—, —(CH$_2$)$_7$—, etc. can be mentioned for the saturated bivalent aliphatic hydrocarbon group, while —CH=CH—, —C(CH$_3$)=CH—, —CH=CH—CH$_2$—, —C(C$_2$H$_5$)=CH—, —CH$_2$—CH=CH—CH$_2$—, —CH$_2$—CH$_2$—CH=CH—CH$_2$—, —CH=CH—CH=CH—CH$_2$—, —CH=CH—CH=CH—CH$_2$—, etc. can be mentioned for the unsaturated bivalent aliphatic hydrocarbon group. A preferably represents a chemical bond or a bivalent aliphatic hydrocarbon group having 1 to 4 carbon atoms, which is preferably a saturated group. More preferably, A represents a chemical bond or —(CH$_2$)$_2$—.

The alkyl group for R$^1$ includes the similar one to the alkyl group for the above-described R$^3$. R$^1$ is preferably hydrogen.

Referring to the formula (I), the partial structural formula:

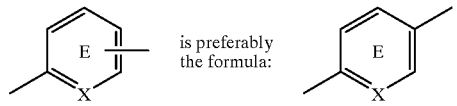

wherein each symbol has the same meanings as described above.

Furthermore, ring E may optionally have 1 to 4 substituents at substitutable positions. Examples of such substituents include an alkyl group, a hydroxy group that may be substituted, halogen, an acyl group that may be substituted, nitro, and an amino group that may be substituted. These substituents may be the same as the substituents mentioned for the hydrocarbon or heterocyclic group for R.

Ring E, namely the partial structural formula:

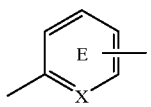 is preferably the formula: 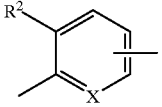

wherein $R^2$ represents hydrogen, an alkyl group, a hydroxy group that may be substituted, halogen, an acyl group that may be substituted, nitro, or an amino group that may be substituted.

The alkyl group, hydroxy group that may be substituted, halogen, acyl group that may be substituted, and amino group that may be substituted, for $R^2$, may each be the same as the substituents mentioned for the hydrocarbon or heterocyclic group for R. $R^2$ is preferably hydrogen, hydroxy group that may be substituted, or halogen. $R^2$ is more preferably hydrogen, or hydroxy group that may be substituted. $R^2$ is especially preferably hydrogen, or a $C_{1-4}$ alkoxy group.

Referring to the formula (I), L and M respectively represent hydrogen or may be combined with each other to form a chemical bond, and preferably they are hydrogen.

The compound in which L and M are combined with each other to form a chemical bond, may exist as (E)- and (Z)-isomers, owing to the double bond at 5-position of the azolidinedione ring.

The compound in which L and M respectively represent hydrogen, may exist as optical isomers, i.e. (R)- and (S)-forms, with respect to the asymmetric carbon at 5-position of the azolidinedione ring. This compound includes these optically active compounds, i.e. (R)- and (S)-forms, as well as the racemic form.

The preferred compound represented by the formula (I) includes the compound in which R represents pyridyl, oxazolyl, or thiazolyl group, optionally having 1 to 3 substituents selected from the group consisting of $C_{1-3}$ alkyl, furyl, thienyl, phenyl, and naphthyl; m is 0; n is 0 or 1; X represents CH; A represents a chemical bond or —$(CH_2)_2$—; $R^1$ represents hydrogen; ring E, namely the partial structural formula:

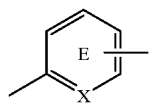 is the formula: 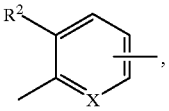, wherein $R^2$ is hydrogen or a $C_{1-4}$ alkoxy group; and L and M represent hydrogen.

Examples of the preferred compound represented by the formula (I) includes

5-[4-[2-(5-ethyl-2-pyridyl)ethoxy]benzyl]-2,4-thiazolidinedione (generic name: pioglitazone);

5-[[4-[(3,4-dihydro-6-hydroxy-2,5,7,8-tetramethyl-2H-1-benzopyran-2-yl)methoxy]phenyl]methyl]-2,4-thiazolidinedione(generic name: troglitazone/CS-045);

5-[[4-[2-(methyl-2-pyridinylamino)ethoxy]phenyl]methyl]-2,4-thiazolidinedione(generic name: rosiglitazone/BRL-49653); and 5-[3-[4-(5-methyl-2-phenyl-4-thiazolylmethoxy]phenyl]propyl]-2,4-oxazolidinedione.

A compound represented by the formula (I) is especially preferably pioglitazone.

A salt of a compound represented by the formula (I) is preferably a pharmacologically acceptable salt, which includes salts with inorganic bases, salts with organic bases, salts with inorganic acids, salts with organic acids, and salts with basic or acidic amino acids.

The preferred salt with an inorganic base includes salts with alkali metal such as sodium, potassium, etc. or alkaline earth metal such as calcium, magnesium, etc.; aluminum salt, and ammonium salts.

The preferred salt with an organic base includes salts with trimethylamine, triethylamine, pyridine, picoline, ethanolamine, diethanolamine, triethanolamine, dicyclohexylamine, N,N-dibenzylethylenediamine, etc.

The preferred salt with an inorganic acid includes salts with hydrochloric acid, hydrobromic acid, nitric acid, sulfuric acid, phosphoric acid, etc.

The preferred salt with an organic acid includes salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, etc.

The preferred salt with a basic amino acid includes salts with arginine, lysine, ornithine, etc. The preferred salt with an acidic amino acid includes salts with aspartic acid, glutamic acid, etc.

A compound represented by the formula (I) or salt thereof is preferably pioglitazone hydrochloride, troglitazone or rosiglitazone (or its maleate), especially preferably pioglitazone hydrochloride.

A compound represented by the formula (I) or salt thereof can be produced in accordance with methods described in JP-A S55(1980)-22636 (EP-A-8203), JP-A S60(1985)-208980 (EP-A-155845), JP-A S61(1986)-286376 (EP-A-208420), JP-A S61(1986)-85372 (EP-A-177353), JP-A S61(1986)-267580 (EP-A-193256), JP-A H5(1993)-86057 (WO-A-92/18501), JP-A H7(1995)-82269 (EP-A-605228), JP-A H7(1995)-101945 (EP-A-612743), EP-A-643050, EP-A-710659, etc, or methods analogous thereto.

Examples of the insulin sensitizer employed in the present invention include, in addition to the above-described compound, (±)-4-[4-[2-(5-methyl-2-phenyloxazol-4-yl)ethoxy]benzyl]isoxazolidin-3,5-dione (JTT-501) or its salt;

5-[[3,4-dihydro-2-(phenylmethyl)-2H-1-benzopyran-6-yl]methyl]-2,4-thiazolidinedione (generic name: englitazone) or its salt (preferably sodium salt);

5-[[4-[3-(5-methyl-2-phenyl-4-oxazolyl)-1-oxopropyl]phenyl]methyl]-2,4-thiazolidinedione (generic name: darglitazone/CP-86325) or its salt (preferably sodium salt);

5-[2-(5-methyl-2-phenyl-4-oxazolylmethyl)benzofuran-5-ylmethyl]-2,4-oxazolidinedione (CP-92768) or its salt;

5-(2-naphthalenylsulfonyl)-2,4-thiazolidinedione (AY-31637) or its salt;

4-[(2-naphthalenyl)methyl]-3H-1,2,3,5-oxathiadiazol-2-oxide (AY-30711) or its salt;

5-[[6-(2-fluorobenzyloxy)-2-naphthyl]methyl]-2,4-thiazolidinedione (MCC-555) or its salt;

(±)-[5-[(2,4-dioxothiazolidin-5-yl)methyl]-2-methoxy-N-[[4-(trifluoromethyl)phenyl]methyl]benzamido (AHG-255) or its salt;

4-[1-(3,5,5,8,8-pentamethyl-5,6,7,8-tetrahydronaphthalen-2-yl)ethenyl]benzoic acid (LGD1069) or its salt;

6-[1-(3,5,5,8,8-pentamethyl-5,6,7,8-tetrahydronaphthalen-2-yl)cyclopropyl]nicotinic acid (LGD100268) or its salt;

1,4-bis[4-[(3,5-dioxo-1,2,4-oxadizolidin-2-yl)methyl]phenoxy]-2-butene (YM-440) or its salt, etc.

Salts of these compounds include those similar to the salt of a compound represented by the formula (I) mentioned above.

An insulin sensitizer is preferably pioglitazone hydrochloride, troglitazone, rosiglitazone (or its maleate), or (±)-4-[4-[2-(5-methyl-2-phenyloxazol-4-yl)ethoxy]benzyl]isoxazolidin-3,5-dione, especially preferably pioglitazone hydrochloride.

An anorectic means any and all drugs that suppresses appetite by acting directly or indirectly on an appetite center. Specific examples of the anorectic include central anorectics and physiologically active peptide related substances.

The central anorectics mean drugs that act on α-adrenaline receptors, β-adrenaline receptors, dopamine receptors, or serotonin receptors to suppress appetite.

Preferred examples of the central anorectics include α-adrenaline receptor antagonists (e.g., yohimbine, etc.), β-adrenaline receptor agonists (e.g., mazindol, amphetamine, dextroamphetamine, phentermine, benzphetamine, methamphetamine, phendimetrazine, phenmetrazine, diethylpropion, sibutramine, phenylpropanolaimine, clobenzorex, etc.), dopamine receptor agonists (e.g., ER-230, doprexin, etc.), serotonin receptor agonists (e.g., dexfenfluramine, fenfluramine, etc.), 5-HT agonists (e.g., (+)norfenfluramine, sertraline, etc.), cimetidine, ergoset, etc.

The physiologically active peptide related substances mean physiologically active peptides acting directly or indirectly on an appetite controller to suppress appetite, their analogues; agonists or antagonists of such physiologically active peptides.

Preferred examples of the physiologically active peptide related substances include leptin and its analogues, leptin receptor agonists, leptin resistance-improving agents, neuropeptide Y (NPY) antagonists (e.g., NGD-95-1, SR-120819-A, PD-160170, 1229-U-91, etc.), cholecystokinin (CCK) agonists (e.g., FPL-15849, GW-5823, GW-7178, GI-248573, AR-R-19021, etc.), glucagon-like peptide 1 (GLP-1) or its analogues or its agonists (e.g., AZM-134, etc.), galannin antagonist, glucagon agonists, melanin-concentrating hormone (MCH) agonists, melanocortin agonists (especially, melanocortin 4 receptor (MC4R) agonists, MC4R/MC3R mixed agonists), enterostatin agonists, tripeptidylpeptidase II inhibitors (e.g., UCL-1397, etc.), corticotropin releasing hormone or its analogues or its agonists (e.g., urocortin, etc.), etc.

An anorectic is preferably central anorectics, more preferably β-adrenaline receptor agonists, especially preferably mazindol.

In the pharmaceutical composition of the present invention, especially preferably employed is a pharmaceutical composition wherein an insulin sensitizer is pioglitazone hydrochloride and an anorectic is mazindol.

A pharmaceutical composition of the present invention can be used as an agent for preventing or treating diabetes. Examples of the diabetes include insulin-dependent diabetes mellitus, noninsulin-dependent diabetes mellitus and etc. A pharmaceutical composition of the present invention is especially preferably employed for noninsulin-dependent diabetes mellitus.

Further, a pharmaceutical composition of the present invention can be used as an agent for preventing or treating diabetic complications (e.g., neuropathy, nephropathy, retinopathy, macroangiopahty, coronary artery diseases, osteopenia, etc.).

Further, a pharmaceutical composition of the present invention can be used as an agent for treating impaired glucose tolerance. Referring to the definition of impaired glucose tolerance, WHO (World Health Organization) suggests a criterion in a 75 g oral glucose tolerance test (75 g OGTT). According to this criterion, impaired glucose tolerance means a condition wherein a fasting glucose level (glucose concentration in venous plasma) is less than 140 mg/dl, and a 2 hr after glucose level (glucose concentration in venous plasma), when a 75 g oral glucose tolerance test is conducted after an overnight fasting, ranges from 140 to 199 mg/dl.

Diabetes means a condition wherein a fasting glucose level (glucose concentration in venous plasma) is 140 mg/dl or more, and a 2 hr after glucose level (glucose concentration in venous plasma), when a 75 g oral glucose tolerance test is conducted after an overnight fasting, is 200 mg/dl or more.

Regarding the criterion of diabetes, new criteria are reported from ADA (American Diabetic Association) on 1997 and from WHO on 1998.

According to these reports, diabetes means a condition wherein a fasting glucose level (glucose concentration in venous plasma) is 126 mg/dl or more, and a 2 hr after glucose level (glucose concentration in venous plasma), when a 75 g oral glucose tolerance test is conducted after an overnight fasting, is 200 mg/dl or more.

According to the above reports, impaired glucose tolerance means a condition wherein a fasting glucose level (glucose concentration in venous plasma) is less than 126 mg/dl, and a 2 hr after glucose level (glucose concentration in venous plasma), when a 75 g oral glucose tolerance test is conducted after an overnight fasting, is 140 mg/dl or more and less than 200 mg/dl.

According to the ADA reports, a condition wherein a fasting glucose level (glucose concentration in venous plasma) is 110 mg/dl or more and less than 126 mg/dl, is called IFG (Impaired Fasting Glucose). According to the WHO report, a condition, among this IFG (Impaired Fasting Glucose), wherein a 2 hr after glucose level (glucose concentration in venous plasma), when a 75 g oral glucose tolerance test is conducted after an overnight fasting, is less than 140 mg/dl, is called IFG (Impaired Fasting Glycemia). The pharmaceutical composition of the present invention can be also used as an agent for preventing or treating diabetes, impaired glucose tolerance, IFG (Impaired Fasting Glucose), IFG (Impaired Fasting Glycemia), all of which is defined by the above new criteria. The pharmaceutical composition of the present invention can also prevent progress to diabetes from impaired glucose tolerance, IFG (Impaired Fasting Glucose) or IFG (Impaired Fasting Glycemia).

Further, a pharmaceutical composition of the present invention can be also used as an agent for preventing or treating diseases such as hyperlipemia, hyperinsulinemia, obesity, hyperphagia, hypertension, cardiovascular diseases (e.g., atherosclerosis, etc.), polycystic ovarian syndrome, gestational diabetes, pancreatitis, glomerulonephritis, glomerular sclerosis, hypertensive nephrosclerosis, and etc., or syndromes (e.g., syndrome X, visceral fat obesity syndrome, etc.) having some of these diseases in combination.

A pharmaceutical composition of the present invention can be obtained by combining active ingredients, an insulin sensitizer and an anorectic. These active ingredients may be subjected to pharmaceutical manufacturing processes by admixing separately or concomitantly with pharmaceutically acceptable carriers in accordance with per se known means [conventional means in fields of pharmaceutical manufacturing techniques, for instance, means described in the Pharmacopoeia of Japan (e.g., Thirteenth Edition, etc.)].

Examples of dosage forms of a pharmaceutical composition of the present invention or its respective active ingredients include oral dosage forms such as tablets, capsules (including soft capsules and microcapsules), powders, granules, syrups, and etc.; and non-oral dosage forms such as injections (e.g., subcutaneous injections, intravenous injections, intramuscular injections, intraperitoneal injections, etc.), external application forms (e.g., nasal spray preparations, transdermal preparations, ointments, etc.), suppositories (e.g., rectal suppositories, vaginal suppositories, etc.), pellets, drip infusions, and etc.

Methods of producing oral dosage forms and non-oral dosage forms are specifically explained below.

Oral dosage forms are produced by adding to the active ingredient(s), for instance, an excipient (e.g., lactose, sucrose, starch, D-mannitol, xylitol, sorbitol, erythritol, crystalline cellulose, light silicic anhydride, etc.), a disintegrator (e.g., calcium carbonate, starch, carboxymethylcellulose, carboxymethylcellulose calcium, low-substituted hydroxypropylcellulose, croscarmellose sodium, carboxymethylstarch sodium, light silicic anhydride, etc.), a binder (e.g., α-starch, gum arabic, carboxymethylcellulose, hydroxypropylcellulose, hydroxypropylmethylcellulose, polyvinylpyrrolidone, crystalline cellulose, methylcellulose, sucrose, D-mannitol, trehalose, dextrin, etc.), or a lubricant (e.g., talc, magnesium stearate, calcium stearate, talc, colloidal silica, polyethylene glycol 6000, etc.), and then compressing and molding the resulting mixture. To the oral dosage form, acids such as hydrochloric acid, phosphoric acid, malonic acid, succinic acid, DL-malic acid, tartaric acid, maleic acid, fumaric acid, citric acid, and etc.; or bases such as sodium carbonate, sodium hydrogencarbonate, sodium citrate, sodium tartrate, and etc. can be added for the purpose of promoting dissolution of the active ingredients).

The oral dosage forms can be coated, by the per se known method, for masking the taste or for enteric dissolution or sustained release. Examples of a coating material that can be employed includes, enteric coating polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, carboxymethylethylcellulose, etc.; gastric coating polymers such as polyvinylacetal diethylaminoacetate, aminoalkyl methacrylate copolymer E, etc.; water-soluble polymers such as hydroxypropylcellulose, hydroxypropylmethylcellulose, etc.; water-insoluble polymers such as ethylcellulose, aminoalkyl methacrylate copolymer RS, ethylacrylate-methylmethacrylate copolymer, etc.; wax, and etc. When coating is carried out, plasticizers such as polyethylene glycol, and etc.; and sunscreens such as titanium oxide, iron sesquioxide, and etc. can be employed together with the above coating material.

Injections can be produced by dissolving, suspending or emulsifying the active ingredient(s) in an aqueous vehicle (e.g., distilled water, physiological saline, Ringer's solution, etc.) or an oily vehicle (e.g., vegetable oil such as olive oil, sesame oil, cottonseed oil, corn oil, etc.; or propylene glycol, macrogol, tricaprylin, etc.) together with a dispersant (e.g., Tween 80 (produced by Atlas Powder, U.S.A.), HCO 60 (produced by Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, D-sorbitol, D-mannitol, xylitol, glucose, fructose, etc.) and etc.

If desired, also employed are additives such as a solubilizer (e.g., sodium salicylate, sodium acetate, polyethylene glycol, propylene glycol, D-mannitol, trehalose, benzyl benzoate, ethanol, trisaminomethane, cholesterol, triethanolamine, sodium carbonate, sodium citrate, etc.), a suspending agent (e.g., surfactants such as stearyltriethanolamine, sodium lauryl sulfate, laurylaminopropionic acid, lecithin, benzalkonium chloride, benzethonium chloride, glyceryl monostearate, and etc.; and hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose, and etc.), a buffering agent (e.g., buffer solutions such as phosphate, acetate, carbonate, citrate, and etc.), a stabilizer (e.g., human serum albumin, etc.), a soothing agent (e.g., propylene glycol, lidocaine hydrochloride, benzyl alcohol, etc.), an antiseptic (e.g., p-hydroxybenzoic acid esters, chlorobutanol, benzalkonium chloride, benzyl alcohol, phenethyl alcohol, dehydroacetic acid, sorbic acid, etc.), and etc.

External application forms can be produced by processing the active ingredient(s) into a solid, semi-solid or liquid composition. For instance, a solid composition is produced by processing the active ingredient(s), either as such or in admixture with an excipient (e.g., lactose, D-mannitol, starch, microcrystalline cellulose, sucrose, etc.), a thickner (e.g., natural gums, cellulose derivatives, acrylic acid polymers, etc.), etc., into powders. The above liquid composition is produced in substantially the same manner as in the case of injections. The semi-solid composition is preferably provided in a hydrous or oily gel form or an ointment form. These compositions may optionally contain a pH control agent (e.g., phosphoric acid, citric acid, hydrochloric acid, sodium hydroxide, etc.), an antiseptic (e.g., p-hydroxybenzoic acid esters, chlorobutanol, benzalkonium chloride, benzyl alcohol, phenethyl alcohol, dehydroacetic acid, sorbic acid, etc.), and etc.

Suppositories can be produced by processing the active ingredient(s) into an oily or aqueous composition, whether solid, semi-solid or liquid. Examples of oleaginous bases that can be used in producing the composition include higher fatty acid glycerides [e.g., cacao butter, Witepsols (huels Aktiengesellschaft, Germany), etc.], medium-chain fatty acid triglycerides [e.g., Migriols(huels Aktiengesellschaft, Germany), etc.], vegetable oils (e.g., sesame oil, soybean oil, cottonseed oil, etc.), etc. Examples of the water-soluble bases include polyethylene glycols, propylene glycol, etc. Further, examples of the hydrophilic bases include natural gums, cellulose derivatives, vinyl polymers, and acrylic acid polymers, etc.

The method for administrating a pharmaceutical composition of the present invention is not limited as long as an insulin sensitizer and an anorectic are combined at the time of administration. Examples of such methods include 1) administration of a single preparation prepared from an insulin sensitizer and an anorectic at the same time; 2) concomitant administration of two kinds of preparations prepared from an insulin sensitizer and an anorectic separately by the same administration route; 3) separate administration of two kinds of preparations prepared from an insulin sensitizer and an anorectic separately by the same administration route; 4) concomitant administration of two kinds of preparations prepared from an insulin sensitizer and an anorectic separately by different administration routes; 5) separate administration of two kinds of preparations prepared from an insulin sensitizer and an anorectic separately by different administration routes (e.g., administration of an insulin sensitizer and an anorectic in this order, or reverse order); and etc. Among others, the above 2) and 3) are preferred.

Preferred embodiments include processing an insulin sensitizer and an anorectic separately into oral dosage forms such as tablets, and administering the oral dosage forms concomitantly or separately.

A pharmaceutical composition of the present invention is low in potential toxicity, and can be safely used in mammals (e.g., human, mouse, rat, rabbit, dog, cat, bovine, equine, swine, monkey, etc.), either orally or non-orally.

The dosage of a pharmaceutical composition of the present invention may be appropriately determined with reference to the dosage recommended for the respective drug(s), and can be selected appropriately according to the subject, the age and body weight of the subject, current clinical status, administration time, dosage form, method of administration, combination of the drug(s), and etc.

The dosage of an insulin sensitizer and an anorectic can be selected appropriately based on clinically used dosage.

For administration of an insulin sensitizer to an adult diabetic patient (body weight: 50 kg), for instance, the dose per day is usually 0.01 to 1000 mg, preferably 0.1 to 500 mg. This dose can be administered once to several times a day. Especially, when pioglitazone hydrochloride is employed as the insulin sensitizer, the dose of pioglitazone hydrochloride per day is usually 7.5 to 60 mg, preferably 15 to 45 mg. When troglitazone is employed as the insulin sensitizer, the dose of troglitazone per day is usually 100 to 1000 mg, preferably 200 to 600 mg. When rosiglitazone (or its maleate) is employed as the insulin sensitizer, the dose of rosiglitazone per day is usually 1 to 12 mg, preferably 2 to 12 mg.

For administration of an anorectic to an adult diabetic patient (body weight: 50 kg), for instance, the dose per day is usually 0.01 to 1000 mg, preferably 0.1 to 500 mg. Especially, when mazindol is employed as the anorectic, the dose of mazindol per day is usually 0.1 to 5 mg, preferably 1 to 3 mg.

The proportion of an insulin sensitizer and an anorectic in a pharmaceutical composition of the present invention can be selected appropriately according to the subject, the age and body weight of the subject, current clinical status, administration time, dosage form, method of administration, combination of the drug(s), and etc. For instance, an anorectic is used in a proportion of usually about 0.0001 to 0.2 weight parts and preferably about 0.001 to 0.02 weight parts relative to one weight part of an insulin sensitizer.

When the pharmaceutical composition of the present invention is administered to a diabetic patient, it provides excellent medicinal properties as compared with administration of an insulin sensitizer or an anorectic alone, for instance, a tendency to decrease the patient's body weight is observed.

The pharmaceutical composition of the present invention is free of apparent detection of side effects such as dependence, hydrodipsia, constipation, nausea, emesis, gastric discomfort, stomach flatulence, dizziness, palpitation, eruption, increase of GTO or GPT, sleep disturbance, etc.

A pharmaceutical composition of the present invention possesses an increased blood sugar lowering action as compared with administration of an insulin sensitizer or an anorectic alone.

Further, a pharmaceutical composition of the present invention possesses an increased blood lipid lowering action or blood insulin lowering action as compared with administration of an insulin sensitizer or an anorectic alone.

Further, a pharmaceutical composition of the present invention possesses an excellent blood sugar lowering action, and therefore, the amount of drugs used can be reduced as compared with administration of an insulin sensitizer or an anorectic alone.

Use of a pharmaceutical composition of the present invention in combination with insulin provides a further excellent blood sugar lowering effect.

Insulin means any and all substances having an insulin action, and exemplified by, for instance, animal insulin extracted from bovine or porcine pancreas; semi-synthesized human insulin which is enzymatically synthesized from insulin extracted from porcine pancreas; and human insulin synthesized by genetic engineering techniques typically using Escherichia coli or yeasts; and etc. Among these, preferred is human insulin synthesized by genetic engineering techniques typically using Escherichia coli or yeasts.

Further, as insulin employed are insulin-zinc containing 0.45 to 0.9 (w/w) % of zinc; protamine-insulin-zinc produced from zinc chloride, protamine sulfate and insulin; and etc.

While insulin is available in a variety of types such as super immediate-acting, immediate-acting, bimodal-acting, intermediate-acting, long-acting, and etc., these types can be appropriately selected according to the patient's condition.

For administration (usually administration in the form of injections) of insulin to an adult patient (body weight: 50 kg), for instance, the dose per day is usually 10 to 100 U (Units), preferably 10 to 80 U (Units).

Use of a pharmaceutical composition of the present invention in combination with insulin enables reduction of the amount of insulin used when compared with the amount used at the time of administration of an insulin alone. Therefore, risk of blood vessel complication and hypoglycemia induction, both of which are evils of large amount insulin administration, is low.

Since a pharmaceutical composition of the present invention possesses an excellent blood sugar lowering action, a satisfactory effect of preventing or treating diabetes can be obtained even if the amount of insulin used is reduced when compared with administration of insulin alone.

Further, use of a pharmaceutical composition of the present invention in combination with insulin secretion enhancers, biguanides, α-glucosidase inhibitors, and etc. provides a more excellent blood sugar lowering effect.

Examples of the insulin secretion enhancers include sulfonylureas. Specific examples of the sulfonylureas include tolbutamide, chlorpropamide, tolazamide, acetohexamide, glyclopyramide or its ammonium salt, glibenclamide, gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, tolcyclamide, glimepiride, etc.

In addition to the above, examples of the insulin secretion enhancers include N-[[4-(1-methylethyl)cyclohexyl] carbonyl]-D-phenylalanine (nateglinide, AY-4166), calcium (2S)-2-benzyl-3-(cis-hexahydro-2-isoindolinylcarbonyl) propionate dihydrate (KAD-1229), repaglinide, etc.

For administration of insulin secretion enhancers to an adult patient (body weight: 50 kg), for instance, the dose per day is usually 0.1 to 1000 mg, preferably 1 to 100 mg.

Examples of the biguanides include phenformin, metformin, buformin, etc.

For administration of biguanides to an adult patient (body weight: 50 kg), for instance, the dose per day is usually 10 to 2500 mg, preferably 100 to 1000 mg.

Examples of the α-glucosidase inhibitors include acarbose, voglibose, miglitol, emiglitate, etc.

For administration of α-glucosidase inhibitors to an adult patient (body weight: 50 kg), for instance, the dose per day is usually 0.1 to 400 mg, preferably 0.6 to 300 mg.

Various kinds of the drugs mentioned above can be used in combination with two or more of them optionally selected. Specific examples of combination when two kinds of drugs are used in combination include "combination of an insulin secretion enhancer and a biguanide", "combination of an insulin secretion enhancer and an α-glucosidase inhibitor", "combination of insulin and a biguanide", "combination of insulin and an α-glucosidase inhibitor", etc.

The blood sugar lowering action of a pharmaceutical composition in the present invention can be evaluated by determining concentration of glucose or Hb (hemoglobin) $A_{1c}$ in venous blood plasma, and then comparing the obtained concentration between before administration and after administration. $HbA_{1c}$ means glycosylated hemoglobin, and is gradually produced in response to blood glucose concentration. Therefore, $HbA_{1c}$ is thought important as an index of blood sugar control which is not easily influenced by rapid blood sugar changes in diabetic patients.

BEST MODE FOR CARRYING OUT THE INVENTION

The following Reference Examples and Examples are intended to describe the present invention in further detail and should by no means be construed as defining the scope of the invention.

REFERENCE EXAMPLE 1

A fluidized-bed granulating and drying machine (produced by Powerex) was charged with 2479.5 g of pioglitazone hydrochloride (2250 g in terms of pioglitazone), 13930.5 g of lactose and 540 g of carboxymethylcellulose calcium (carmellose calcium), followed by mixing at the preheating temperature and spraying 7500 g of an aqueous solution containing 450 g of hydroxypropylcellulose to yield granules. 16820 g of the granules were processed with cutter-mill (produced by Showa Kagaku Kikai Kousakusho) to yield milled granules. 16530 g of the milled granules, 513 g of carmellose calcium and 57 g of magnesium stearate were mixed to yield mixed powders by using a tumbling mixer (produced by Showa Kagaku Kikai Kousakusho). 16800 g of the mixed powders were tabletted by using a tabletting machine (produced by Kikusui Seisakusho) to yield 140000 tablets having the following composition and each containing 15 mg of pioglitazone.

| Composition per tablet (Unit: mg): | |
|---|---|
| 1) Pioglitazone hydrochloride | 16.53 |
| 2) Lactose | 92.87 |
| 3) Carmellose calcium | 7.2 |
| 4) Hydroxypropylcellulose | 3.0 |
| 5) Magnesium stearate | 0.4 |
| Total: | 120.0 |

REFERENCE EXAMPLE 2

In the similar manner to Reference Example 1, 140000 tablets having the following composition and each containing 30 mg of pioglitazone were obtained.

| Composition per tablet (Unit: mg): | |
|---|---|
| 1) Pioglitazone hydrochloride | 33.06 |
| 2) Lactose | 76.34 |
| 3) Carmellose calcium | 7.2 |
| 4) Hydroxypropylcellulose | 3.0 |
| 5) Magnesium stearate | 0.4 |
| Total: | 120.0 |

REFERENCE EXAMPLE 3

In the similar manner to Reference Example 2, 140000 tablets having the following composition and each containing 45 mg of pioglitazone were obtained.

| Composition per tablet (Unit: mg): | |
|---|---|
| 1) Pioglitazone hydrochloride | 49.59 |
| 2) Lactose | 114.51 |
| 3) Carmellose calcium | 10.8 |
| 4) Hydroxypropylcellulose | 4.5 |
| 5) Magnesium stearate | 0.6 |
| Total: | 180.0 |

EXAMPLE 1

Effects of concomitant administration of pioglitazone hydrochloride and mazindol in noninsulin-dependent diabetic mellitus (NIDDM) patients were studied.

When pioglitazone hydrochloride (45 mg/day, oral administration) was concomitantly administered to a NIDDM patient [one sample(man); 44 years old; body weight 99.0 kg; fasting blood sugar 242.0 mg/dl; $HbA_{1c}$ 11.0%] under treatment with mazindol (1.0 mg/day, oral administration) over the period of 8 weeks, fasting blood sugar decreased by 70.0 mg/dl, $HbA_{1c}$ decreased by 2.00%, and body weight decreased by 1.00 kg.

When placebo (oral administration) was administered to NIDDM patients [55 samples (20 men and 35 women); 37 to 73 years old (57.9±8.7 (means±standard deviation) years old; body weight 59.8±12.1 (means±standard deviation of 54 samples) kg; fasting blood sugar 180.1 ±23.0 (means±standard deviation) mg/dl; $HbA_{1c}$ 8.8±1.3 (means±standard deviation) %] over the period of 12 ±2 weeks, fasting blood sugar increased by 3.4±27.3 mg/dl (means±standard deviation of 55 samples), $HbA_{1c}$ increased by 0.45±0.86% (means±standard deviation of 54 samples), and body weight decreased by 0.19±1.21 kg (means±standard deviation of 55 samples).

When pioglitazone hydrochloride (45 mg/day, oral administration) was administered alone to NIDDM patients [50 samples (24 men and 26 women); 23 to 78 years old (55.8 ±10.7 (means±standard deviation) years old; body weight 62.7±10.5 (means±standard deviation) kg; fasting blood sugar 190.5±31.1 (means±standard deviation) mg/dl; $HbA_{1c}$ 9.3±1.6 (means±standard deviation of 49 samples) %] over the period of 12±2weeks, body weight increased by 0.72±2.06 kg (means±standard deviation of 50 samples).

When placebo (oral administration) was concomitantly administered to a NIDDM patient [one sample(woman); 51 years old; body weight 60.0 kg; fasting blood sugar 200.0 mg/dl; $HbA_{1c}$ 9.3%] under treatment with mazindol (0.5 mg/day, oral administration) over the period of 12 weeks, the body weight change was 0.00 kg.

Thus, administration of pioglitazone hydrochloride in combination with mazindol provided an excellent blood sugar lowering action, and a tendency to decrease body weight as compared with administration of pioglitazone hydrochloride or mazindol alone, which confirmed that the pharmaceutical composition of the present invention possesses excellent medicinal properties.

Industrial Applicability

A pharmaceutical composition of the present invention is useful as an agent for preventing or treating diabetes, an agent for preventing or treating diabetic complications, and an agent for treating impaired glucose tolerance, without apparent detection of side effects.

Further, a pharmaceutical composition of the present invention possesses an increased blood sugar lowering action, blood lipid lowering action or blood insulin lowering action as compared with administration of an insulin sensitizer or an anorectic alone.

Further, a pharmaceutical composition of the present invention possesses an excellent blood sugar lowering action, and therefore, the amount of drugs used can be reduced as compared with administration of an insulin sensitizer or an anorectic alone.

What is claimed is:

1. A method for treating diabetes in a mammal in need thereof, which comprises administering to said mammal an effecting amount of an insulin sensitizer selected from the group consisting of pioglitazone, troglitazone, rosiglitazone and 4-[4-[2-(5-methyl-2-phenyloxazol-4-yl)ethoxy]benzyl]isoxazolidin-3,5-dione, or a salt thereof, in combination with sibutramine or mazindol.

2. A method for treating diabetic complications in a mammal in need thereof, which comprises administering to said mammal an effective amount of an insulin sensitizer selected from the group consisting of pioglitazone, troglitazone, rosiglitazone and 4-[4-[2-(5-methyl-2-phenyloxazol-4-yl)ethoxy]benzyl]isoxazolidin-3,5-dione, or a salt thereof, in combination with sibutramine or mazindol.

3. A method for treating impaired glucose tolerance in a mammal in need thereof, which comprises administering to said mammal an effective amount of an insulin sensitizer selected from the group consisting of pioglitazone, troglitazone, rosiglitazone and 4-[4-[2-(5-methyl-2-phenyloxazol-4-yl)ethoxy]benzyl]isoxazolidin-3,5-dione, or a salt thereof, in combination with sibutramine or mazindol.

4. A pharmaceutical composition which comprises pioglitazone, troglitazone, rosiglitazone or 4-[4-[2-(5-methyl-2-phenyloxazol-4-yl)ethoxy]benzyl]isoxazolidin-3,5-dione, or a salt thereof, in combination with sibutramine.

5. A pharmaceutical composition which comprises pioglitazone, troglitazone, rosiglitazone or 4-[4-[2-(5-methyl-2-phenyloxazol-4-yl)ethoxy]benzyl]isoxazolidin-3,5-dione, or a salt there of, in combination with mazindol.

6. The method according to claim 1, wherein pioglitazone or a salt thereof is administered in combination with sibutramine.

7. The method according to claim 1, wherein pioglitazone or a salt thereof is administered in combination with mazindol.

8. The method according to claim 1, wherein rosiglitazone or a salt thereof is administered in combination with sibutramine.

9. The method according to claim 1, wherein rosiglitazone or a salt thereof is administered in combination with mazindol.

10. The method according to claim 2, wherein pioglitazone or a salt thereof is administered in combination with sibutramine.

11. The method according to claim 2, wherein pioglitazone or a salt thereof is administered in combination with mazindol.

12. The method according to claim 2, wherein rosiglitazone or a salt thereof is administered in combination with sibutramine.

13. The method according to claim 2, wherein rosiglitazone or a salt thereof is administered in combination with mazindol.

14. The method according to claim 3, wherein pioglitazone or a salt thereof is administered in combination with sibutramine.

15. The method according to claim 3, wherein pioglitazone or a salt thereof is administered in combination with mazindol.

16. The method according to claim 3, wherein rosiglitazone or a salt thereof is administered in combination with sibutramine.

17. The method according to claim 3, wherein rosiglitazone or a salt thereof is administered in combination with mazindol.

18. The method according to claims 1, 2 or 3, wherein the insulin sensitizer is administered to the mammal separately from sibutramine or mazindol.

19. The method according to claims 1, 2 or 3, wherein the insulin sensitizer is administered to the mammal concomitantly with sibutramine or mazindol.

* * * * *

UNITED STATES PATENT AND TRADEMARK OFFICE
CERTIFICATE OF CORRECTION

PATENT NO.   : 6,329,403 B1
DATED        : December 11, 2001
INVENTOR(S)  : Hiroyuki Odaka and Masahiro Yamane It is certified that error appears in the above-identified patent and that said Letters Patent is hereby corrected as shown below:

<u>Column 19,</u>
Line 29, delete "effecting amount" and insert -- effective amount --.

Signed and Sealed this

Third Day of February, 2004

JON W. DUDAS
*Acting Director of the United States Patent and Trademark Office*